United States Patent [19]

Schachar

[11] Patent Number: 4,526,171
[45] Date of Patent: Jul. 2, 1985

[54] CORNEA INCISION DEVICE

[76] Inventor: Ronald A. Schachar, 1020 N. Highway 75, Denison, Tex. 75020

[21] Appl. No.: 112,328

[22] Filed: Jan. 15, 1980

[51] Int. Cl.³ .............................................. A61B 17/32
[52] U.S. Cl. ................................................... 128/305
[58] Field of Search ............. 128/305, 305.1, 751-754, 128/253, 302, 315; 30/315, 294; 294/1 CA

[56] References Cited

U.S. PATENT DOCUMENTS 3,074,407  1/1963  Moon et al. .................... 128/303 R
3,743,337  7/1973  Crary ............................... 294/1 CA
4,205,682  6/1980  Crock et al. ....................... 128/305

FOREIGN PATENT DOCUMENTS 2849011  6/1979  Fed. Rep. of Germany ...... 128/326

Primary Examiner—Michael H. Thaler
Attorney, Agent, or Firm—Jerry W. Mills; Gregory M. Howison

[57] ABSTRACT

This invention relates to correcting vision defects and more particularly to changing the curvature of the human cornea by the formation of incisions on the surface of the cornea.

22 Claims, 4 Drawing Figures

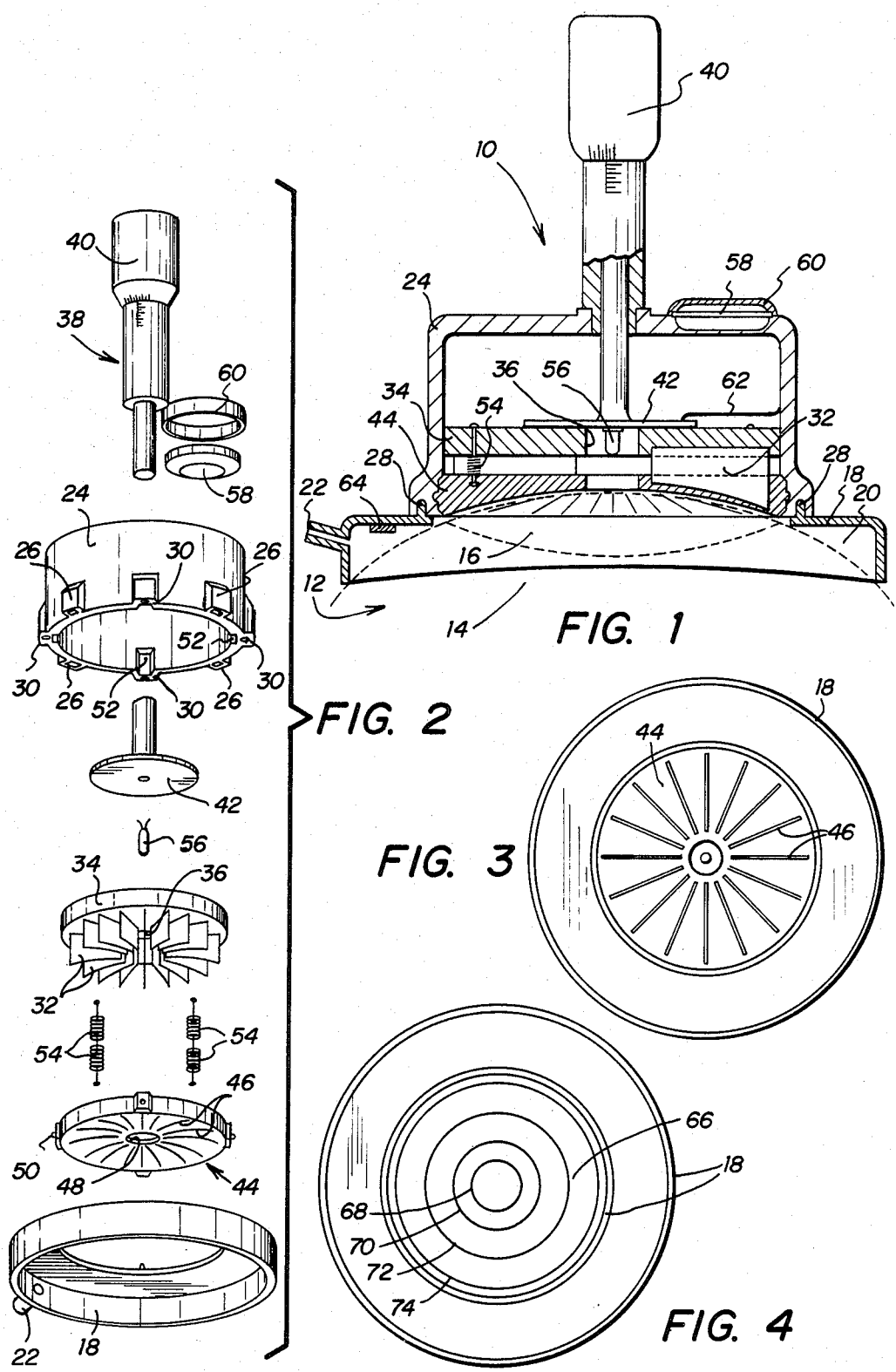

CORNEA INCISION DEVICE

BACKGROUND ART

Ophthalmologists have long been concerned with correct hyperopia in the human eye and defects which relate to the curvature of the cornea. Well-known methods of correcting hyperopia and myopia include corrective lenses, such as eyeglasses or contact lenses. These methods have obvious drawbacks as they do not form an integral part of the eye structure. Eyeglasses and contact lenses are often bothersome to wear and are subject to loss or breakage. Contact lenses also present additional problems such as eye infections and corneal damage relating to excessive abrasion or scratching.

One surgical method that has developed includes the formation of incisions on the surface of the cornea made to a desired depth and location to change the curvature of the cornea. For example, a series of surface incisions are made extending radially from the center of the cornea to the edge of the cornea. Generally, the incisions are not made over an area defined by approximately a three millimeter diameter circle in the center of the cornea. This is due to the fact that the surface incisions cause the cornea to bulge at the site of the incision and it is generally desired to cause the periphery of the cornea to bulge outwardly with respect to its central portion. Further, it is not desirable to form incisions over the primary viewing area of the cornea.

The following criteria are used to determine the depth, length and location of the surface incisions to produce the desired change of curvature to thereby produce the desired correction:
1. thickness of the cornea;
2. intraocular pressure;
3. elasticity of the cornea;
4. refractive error; and
5. curvature of the cornea.

Generally, it is desired that the ratio of the depth of the incision to the thickness of the cornea be constant along the length of the incision. Typically, the depth of the incisions will be equivalent to between about 50 and 75% of the corneal thickness. The cornea does not have a uniform thickness and the thickness of the cornea at the center is generally about one half the thickness of the peripheral portions of the cornea. Therefore, for the ratio of the incision depth to corneal thickness to be constant, the depth of the incision must increase as it extends away from the center of the cornea.

While such surgical techniques offer great promise in correcting vision, heretofore each operation has required a surgeon to make a series of individual incisions. This is not only time consuming, but it is difficult to make the proper pattern of incisions. Moreover, the eye is often difficult to operate on due to the flexible nature of the eye.

A need therefore exists for a device that can reliably and safely form incisions having the desired location, depth and length so that the desired change in the radius of curvature of the cornea can be attained.

DISCLOSURE OF THE INVENTION

In accordance with one embodiment of the present invention, a device is provided for performing an operation on the cornea which increases the cornea's radius of curvature. The device allows incisions to be formed on the surface of the cornea in the desired locations of the desired depth and length.

The apparatus according to the invention includes a suction ring dimensioned to concentrically surround the cornea while forming a volume concentric with the cornea and bounded by the ring and the sclera of the eye. A passageway communicates with the closed volume and allows application of a vacuum thereto to maintain the ring in a fixed position with respect to the eye and increase the relative intraocular pressure during the formation of the desired incisions. Application of the vaccum to the eye adjacent increases the tension of the cornea to facilitate formation of the surface incisions and secure the suction ring on the eye.

A housing assembly is dimensioned to fit on the suction ring and is securable thereto in a fixed position. A plurality of cutting blades for forming the incisions are mounted on a blade platform that is movably mounted within the housing for movement to and away from the eye. The blades are mounted in a pattern corresponding with the desired pattern of incisions. A screw micrometer drive is utilized to advance the blade platform towards the cornea so that the amount of penetration by the cutting blades into the cornea can be controlled to achieve incisions having the desired depth.

A stationary disc having a concave surface approximating the curvature of the eye is mounted in the housing so that when the housing is placed on the suction ring over an eye, the concave surface of the disc superimposes the cornea. The disc has slots therein corresponding with the array of cutting blades mounted in the blade platform for allowing movement of the blades through the slots and into the cornea. The blade platform and disc are interconnected by springs so that a force is exerted between the disc and base causing the cutting blades and base to retract from the cornea by reversing the direction of the micrometer drive after the incisions have been formed, and for maintaining the blade platform in contact with the micrometer drive. The blade platform and disc are removable for changing cutting blades and allowing the use of alternate cutting blade patterns.

The blade platform and disc each contain an aperture that extends longitudinally through the center of each so that a light source may be incorporated in the device to impinge upon the subject's eye. By looking at the light source, the eye of the subject is properly positioned with respect to the device so that the incisions can be made in a known relationship with respect to the center of the cornea.

In accordance with an alternate embodiment of the present invention, a device is provided for performing an operation on the cornea which decreases the cornea's radius of curvature. This device is similar to the previously described embodiment except that the cutting blades form a series of spaced apart concentric rings for forming concentric circular surface incisions on the cornea. In this embodiment, the stationary disc is not utilized.

BRIEF DESCRIPTION OF THE DRAWINGS

The invention can be more completely understood by reference to the accompanying drawings in which:

FIG. 1 is a side elevational view, partly in section, along lines 1—1 of FIG. 3 of a device in accordance with the invention;

FIG. 2 is an exploded perspective view of the device depicted in FIG. 1;

FIG. 3 is a bottom elevational view of the device shown in FIG. 1; and

FIG. 4 is a bottom elevational view of an alternate embodiment according to the present invention.

DESCRIPTION OF THE PREFERRED EMBODIMENT

Referring generally to the drawings, and in particular to FIG. 1, there is depicted a cornea incision device in accordance with the invention, generally referred to by reference numeral 10. Also depicted in FIG. 1 is a side elevational view of part of a human eye 12 that includes a sclera 14 and a cornea 16.

Suction ring 18 concentrically surrounds cornea 16 and abuts sclera 14 as shown in FIG. 1. Suction ring 18 abuts sclera 14 along the inner circumference of suction ring 18 and along the terminal portion of downwardly extending flange 19 of suction ring 18 to form a sealed volume 20 bounded by suction ring 18 and that portion of sclera 14 covered by suction ring 18. An air passageway 22 communicates with sealed volume 20 to allow application of a vacuum to sealed volume 20. By application of a vacuum to sealed volume 20 the observed and relative intraocular pressure of eye 12 will increase the tension of cornea 16 facilitating formation of the incisions and restricting movement of eye 12 with respect to suction ring 18. Depending on the desired location of the surface incisions, the inner diameter of suction ring 18 may be either larger or smaller than the diameter of cornea 16, although as depicted in FIG. 1, the inner diameter of suction ring 18 will generally be larger than the diameter of cornea 16. The preferred inner diameter of suction ring 18 is about 14.5 millimeters and the preferred outer diameter is about 22 millimeters.

A housing 24 is adapted to rest upon the top portion of suction ring 18. Housing 24 is secured to suction ring 18 by means of magnets 26 located on the periphery of housing 24 for attachment to suction ring 18. In addition, a plurality of pins 28 extend upwardly from suction ring 18 for engagement with a plurality of complementary holes 30 located on the periphery of housing 24 to provide the desired alignment of housing 24 with suction ring 18. The combination of magnets and pin-hole engagements retains housing on suction ring 18 during the surgical procedure. Housing 24 is removed from suction ring 18 merely by applying sufficient force to overcome the magnetic force generated by magnets 26 that retain housing 24 on suction ring 18 and any frictional resistance between pins 28 and holes 30.

Housing 24 is preferably cylindrical in shape although any desired shape may be employed as long as housing 24 is securable to suction ring 18 while providing proper alignment of the cutting blades, as will be hereinafter described.

Generally, cornea incision device 10 incorporates a plurality of cutting blades 32 that are arrayed in a configuration so that movement of the blades towards the cornea produces the desired pattern of surface incisions. However, it is to be recognized that under some circumstances only a single cutting blade would be utilized. As illustrated in FIGS. 1 and 2, cutting blades 32 are carried by blade platform 34. Blade platform 34 is preferably circular in shape with cutting blades 32 being mounted on the side of blade platform 34 that faces cornea 16. Blade platform 34 preferably includes therein a hole 36 that extends through the center of blade platform 34, the purpose of which will be hereinafter described. Blade platform 34 is mounted within housing 24 as shown in FIG. 1 for movement axially of housing 24 to and away from cornea 16. Movement of blade platform 34 and therefore cutting blades 32 towards cornea 16 is effected by micrometer drive 38 that includes micrometer 40 and micrometer contact plate 42. Contact plate 42 moves axially of housing 24 when micrometer 40 is turned. Contact plate 42 is in operative relation to blade platform 34 for exerting a downward force on blade platform 34 thereby moving cutting blades 32 towards cornea 16 eventually causing cutting blades 32 to form the desired incisions in cornea 16.

A stationary disc or an eye cup 44 is secured within housing 24 at the bottom portion thereof, as illustrated in FIG. 1. Eye cup 44 has a concave surface facing cornea 16 that approximates the curvature of the cornea so that the concave surface of eye cup 44 superimposes cornea 16 during the surgical procedure. Eye cup 44 is preferably circular in shape and is best illustrated in FIG. 3, eye cup 44 includes slots 46 that are complementary with the array of cutting blades 32. Eye cup 44 also preferably includes a hole 48 for purposes which will be hereinafter described. Eye cup 44 is secured within housing 24 by any suitable arrangement. In the illustrated form, eye cup 44 is secured within housing 24 by a snap-lock arrangement in which a plurality of snap-lock projections 50 are located on the periphery of eye cup 44 for insertion into complementary slots 52 located interiorly of housing 24, which preferably allows for removal of eye cup 44 and blade platform 34 for utilizing different cutting blade arrays, and for sterilizing component parts of the device.

Cornea incision device 10 includes an assembly for retraction of cutting blades 32 after formation of the surface incisions and for maintaining blade platform in contact with contact plate 42 of micrometer drive 38. Blade platform 34 is spring-biased so that an upward force is exerted upon blade platform 34 sufficient to retract cutting blades 32 from cornea 16 after completion of the desired incisions and to maintain blade platform 34 in contact with contact plate 42 as contact plate 42 is moved away from cornea 16 by micrometer 40. In the preferred embodiment, four springs 54 are mounted between blade platform 34 and eye cup 44 so that springs 54 are in compression whenever any portion of cutting blades 32 extend beyond the concave surface of eye cup 44 for providing a sufficient force to maintain blade platform 34 in contact with contact plate 42 of micrometer drive 38.

In the preferred embodiment, cornea incision device 10 allows for alignment with respect to the center of cornea 16. A light source 56 is provided and preferably located within housing 24 along the central axis of blade platform 34 and eye cup 44. In the illustrated embodiment, light source 56 is mounted on contact plate 42 so that a light beam impinges on cornea 16 along the central axis of blade platform 34 and eye cup 44. Thus, the eye can be centered with respect to suction ring 18 and housing 24 by means of light source 56 by directing the patient to focus on light source 56. A battery 58 is mounted in housing 24 to provide a source of electrical energy for light source 56 and can be secured in housing 24 by snap-lock cover 60, for example. An electrical connection 62 transmits electrical energy from battery 58 to light source 56. Battery 58 may form an electrical connection with light source 56 by any suitable method.

Optionally a pressure transducer 64 may be incorporated into suction ring 18 to monitor the pressure in sealed volume 20. Alternatively, a pressure transducer may be incorporated in eye cup 44 to monitor the intraocular pressure of eye 12.

Micrometer 40 is calibrated so that the distance that cutting blades 32 extend past eye cup 44 can be regulated and determined by setting micrometer 40 to the desired value. Generally, the preferred pattern of cutting blades 32 for reducing the curvature of the cornea will be as shown in the FIGS. 1-3, that is, cutting blades are radially oriented with approximately a three millimeter diameter circle located at the center of blade platform 34 having no cutting blades disposed therein so that approximately a three millimeter diameter circle on the center of the cornea will not have any incisions formed therein. Surface incisions are generally not formed over the central portion of the cornea, since if the overall shape of the cornea is to be flattened, the peripheral portions of the cornea should bulge outwardly with respect to the central portion of the cornea and therefore no surface incisions are made in the central portion of the cornea. Generally and in the illustrated embodiment, the shape of each of cutting blades 32 is such that the cutting edge of the blade is curved so that the incision is shallowest at the point nearest to the center of the cornea and progressively deepens as the incision extends towards the periphery of the cornea. Such a blade configuration is generally required since the cornea is thinnest at the central portion and progressively thickens from the central portion to the peripheral portions thereof. Since the incision depth is more critical near the central portion of the cornea than near its periphery, the depth of blade penetration as calibrated by micrometer 40 will be measured from the closest point of the incision to the center of the cornea.

The following is a general description illustrating use of cornea incision device 10 during a surgical procedure for forming surface incisions in human cornea 16 to alter the radius of curvature. Suction ring 18 is placed on sclera 14 of eye 12 so that suction ring 18 surrounds cornea 16. The remainder of cornea incision device 10 is then secured to suction ring 18. This may be done prior to placing suction ring 18 on sclera 14. The patient is then directed to fixate on light source 56 causing the middle of eye 12's visual axis to be aligned with the longitudinal axis of cornea incision device 10 thereby centering suction ring 18 and cutting blades 32 with respect to cornea 16.

A vacuum is then applied to sealed volume 20 by means of a vacuum source (not shown) communicating with sealed volume 20 via air passageway 22. Preferably, the pressure in sealed volume 20 will be reduced by about 50 to 65 mm Hg. This has the effect of increasing the relative intraocular pressure thereby tensioning the cornea and facilitating formation of the surface incisions. Either the pressure in sealed volume 20 may be monitored, by means of pressure transducer 64, or housing 24 together with the elements contained therein may be removed from suction ring 18 and the intraocular pressure can be monitored utilizing, for example, an applanator tonometer. Application of a vacuum to sealed volume 20 causes suction ring to adhere to that portion of eye 12 on which it rests so that eye 12, will not move relative to suction ring 18. After the desired vacuum has been attained, housing 24 is replaced on suction ring 18 (if housing 24 was removed to measure intraocular pressure). Blade platform 34 carrying cutting blades 32 is then advanced towards cornea 16 until the desired depth of the surface incisions are attained. After forming the desired surface incisions, the direction of travel of blade platform 34 and cutting blades 32 is reversed by reversing the direction of micrometer 40, springs 54 causing blade platform 34 and cutting blades 32 to retract from cornea 16 sufficiently so that no portion of cutting blades 32 extends past the concave surface of eye cup 44. The vacuum is then terminated and cornea incision device 10 is removed from the surface of sclera 14.

Both blade platform 34 carrying cutting blades 32 and eye cup 44 are removable from housing 24 and may be replaced by another blade platform carrying cutting blades that may be arrayed in a different pattern together with an eye cup corresponding with the new cutting blade array thereby allowing the formation of the desired pattern of surface incisions.

In accordance with an alternate embodiment of the present invention, there is illustrated in FIG. 4 an array of cutting blades mounted in a blade platform 66 for forming incisions in a human cornea that cause the curvature of the cornea to increase. Blade platform 66 is similar in construction to blade platform 34 previously described. In this embodiment, an eye cup is not utilized because of the blade configuration. A plurality of cutting blades, 68, 70, 72 and 74 are mounted on blade platform 66 to form a series of concentric circular spaced apart at predetermined distances for forming a series of concentric, circular ring incisions on the surface of a cornea. Preferably, blade 68 forms a circular ring having a diameter of approximately 3 millimeters. Each of cutting blades 68, 70, 72 and 74 are aligned so that they concentrically surround the center of the cornea. Thus, as in the previously described embodiment, no incisions are made in in the central three millimeter diameter portion of the cornea, since it is generally undesirable to form surface incisions over the primary viewing area of the cornea. In this embodiment, since an eye cup is not utilized, it is contemplated that a spring force for retracting the blades after an incision has been made could be provided by mounting springs between the top of blade platform 66 and the housing so that the springs exert an upward force on blade platform 66 to keep blade platform 66 in contact with micrometer contact plate 42 as previously described.

While the invention has been described with respect to its preferred embodiments, it is evident that numerous changes, modifications and substitutions may be made without departing from the scope of the appended claims. Although, as described herein, this embodiment utilized four circular blades, it is to be understood that any suitable number of blades may be utilized.

I claim:

1. A device for forming surface incisions of a desired pattern and depth on the cornea of an eye comprising:
    (a) a housing;
    (b) at least two cutting blades in a predetermined array for producing a desired pattern of surface incisions;
    (c) means for positioning said housing in an operative position over the eye;
    (d) a blade platform contained within said housing, said blade platform having said cutting blades mounted thereto in said array;
    (e) means for guiding and advancing said blade platform in a direction towards and into the surface of the cornea to simultaneously incise a plurality of incisions in accordance with the predetermined pattern of said array, said direction being substantially normal to the cornea surface at the cornea center;

(f) means for controlling the depth of the incisions; and (g) means for retracting said cutting blades from said cornea after forming the incisions.

2. The device of claim 1 and further comprising: means for applying a partial vacuum to the sclera adjacent the cornea while forming the incisions.

3. The device as recited in claim 2 wherein said housing positioning means comprises a circular ring adapted to fit on an eye and concentrically surround the cornea, said ring having a flange extending axially from the outer periphery of said ring adapted to rest on the sclera of the eye thereby forming a closed volume between the ring and the sclera when said ring is in position on an eye, said ring including means for mounting said housing on said ring and said ring having an air passageway extending through said ring allowing application of a partial vacuum to said closed volume.

4. The device as recited in claim 1 wherein said means for controlling the depth of the incisions includes micrometer means for advancing said blade platform.

5. The device as recited in claim 1 wherein said retracting means includes spring means for applying a force on said base plate in a direction away from the cornea.

6. The device as recited in claim 1 further comprising an eye cup having a concave surface approximating the curvature of the eye fixedly mounted in said housing so that when said housing is in the operative position over the eye, the concave surface of said eye cup superimposes the cornea, said eye cup having slots therein corresponding with the array of cutting blades mounted in said blade platform for allowing movement of said blades through the slots and into the cornea.

7. The device as recited in claim 6 wherein said means for retracting said cutting blades comprises spring means mounted between said eye cup and said blade platform for exerting a force between said eye cup and said blade platform.

8. The device as recited in claim 1 further comprising means for aligning said device with the center of the cornea.

9. The device as recited in claim 8 wherein said alignment means comprises a light source mounted within said housing and located so that when the eye of the patient focuses on said light source, the cornea is in alignment with said cutting blades.

10. The device as recited in claim 1 wherein said blades are removable from the device to allow different blades to be utilized in the device.

11. A device for forming surface incisions of a desired pattern and depth on the cornea of an eye comprising:

(a) a cylindrical housing having a top and bottom of said housing adjacent the cornea so that the longitudinal axis of said housing is normal to and intersects the center of the cornea;

(c) at least two cutting blades for forming the incisions;

(d) a blade platform coaxially mounted within said housing having a top and bottom oriented correspondingly to the top and bottom of said housing for carrying said cutting blades, said blades being rigidly secured to the bottom of said platform, said platform being movable axially of said housing to allow said blades to simultaneously penetrate the cornea to the desired depth, thereby simultaneously incising a plurality of incisions corresponding to the desired pattern and number of said blades rigidly secured to said platform; and (e) means for moving said blade platform a known distance axially of said housing and for retracting said cutting blades after forming the incisions.

12. The device of claim 11 further comprising: means for applying a partial vacuum to the sclera adjacent the cornea while forming the incisions.

13. The device as recited in claim 11 wherein said means for moving said blade platform axially a known distance and for retracting said blades after forming the incisions includes a micrometer screw drive to move said platform and spring means for applying a force on said platform to retract said blades.

14. The device as recited in claim 11 further comprising a circular eye cup having a concave surface for superimposing the cornea, said eye cup being removeably secured coaxially within said housing and said eye cup having an array of slots extending therethrough corresponding with the pattern of cutting blades mounted on said blade platform to allow movement of said blades through the slots and into the cornea.

15. The device as recited in claim 14 wherein said means for moving said blade platform a known distance axially of said housing includes a micrometer screw drive mounted to said housing and spring means for maintaining said blade platform in operative relation to said micrometer screw drive.

16. The device as recited in claim 11 wherein said positioning means comprises a circular ring adapted to fit on an eye and concentrically surround the cornea, said ring having a flange extending axially from the outer periphery of said ring adapted to rest on the sclera of the eye to permit application of a partial vacuum to that portion of the eye adjacent said ring for increasing the apparent intraocular pressure of the eye and tensioning the cornea to facilitate formation of the surface incisions.

17. The device as recited in claim 16 further comprising pressure transducer means to monitor the vacuum applied to that portion of the eye adjacent to said ring.

18. The device recited in claim 11 further comprising a light source for directing light along the longitudinal axis of said housing for impingement on the cornea.

19. The device as recited in claim 18 wherein said light source is a light emitting diode.

20. The device as recited in claim 11 wherein said blades extend radially with respect to the center of the cornea.

21. The device as recited in claim 11 wherein said blades are arrayed in a plurality of concentric circular rings with respect to the center of the cornea.

22. The device as recited in claim 11 wherein said blades are removable from the device to allow different blades to be utilized in the device.

* * * * *